United States Patent [19]

Mueller et al.

[11] Patent Number: 5,002,967

[45] Date of Patent: Mar. 26, 1991

[54] PHENOLIC THIOETHERS, SULFOXIDES, AND DISULFIDES AS INHIBITORS OF 5-LIPOXYGENASE

[75] Inventors: Richard A. Mueller, Glencoe; Richard A. Partis, Evanston, both of Ill.

[73] Assignee: G. D. Searle & Co., Chicago, Ill.

[21] Appl. No.: 378,687

[22] Filed: Jul. 11, 1989

Related U.S. Application Data

[63] Continuation of Ser. No. 58,457, Jun. 5, 1987, abandoned.

[51] Int. Cl.$^5$ .............. A61K 31/19; A61K 31/34; A61K 31/35; A61K 31/235
[52] U.S. Cl. .............. 514/473; 514/460; 514/532; 514/570; 514/826; 549/273; 549/323; 560/9; 560/11; 560/17; 562/426; 562/429; 562/431
[58] Field of Search .............. 514/532, 570, 460, 473; 562/426, 429, 431; 560/9, 11, 17; 549/273, 323

[56] References Cited

U.S. PATENT DOCUMENTS

| | | | |
|---|---|---|---|
| 3,392,194 | 7/1968 | Waring et al. | 260/516 |
| 3,624,143 | 11/1971 | Shen et al. | 260/516 |
| 3,652,646 | 3/1972 | Leight et al. | 260/473 G |
| 4,012,523 | 3/1977 | Wagner | 560/11 X |
| 4,029,812 | 6/1977 | Wagner et al. | 424/298 |
| 4,153,803 | 5/1979 | Thiel | 560/17 |
| 4,528,286 | 7/1985 | Moller et al. | 514/332 |
| 4,534,874 | 8/1985 | Steinberg et al. | 252/51.5 A |
| 4,663,333 | 5/1987 | Mueller et al. | 514/346 |
| 4,711,903 | 12/1987 | Mueller | 514/381 |
| 4,755,524 | 7/1988 | Mueller et al. | 514/381 |

FOREIGN PATENT DOCUMENTS

| | | |
|---|---|---|
| 86101299.5 | 9/1980 | European Pat. Off. . |
| 2716125 | 3/1984 | European Pat. Off. . |
| 86101296.1 | 3/1986 | European Pat. Off. . |
| 86101300.1 | 12/1986 | European Pat. Off. . |
| 1936463 | 3/1989 | Fed. Rep. of Germany . |
| 57-58663 | 5/1982 | Japan . |

OTHER PUBLICATIONS

Chem. Abstracts, 90:151802x (Tsuda) 1979.
Chem. Abstracts, 94:30290c.
M. B. Neuworth, J. Med. Chem., 13 (4): 722–725 (1970).
Chem. Abstracts 109226y.
Chem. Abstracts 84:6258w.
Chem. Abstracts 83:27876r.
Medvedev et. al., Izv. Vyssh. Uchenbn. Zaved., Khim. Khim. Tekhnol., 20, 568–574 (1977).
Bengt Samuelsson, "Leukotrienes: Mediators of Immediate Hypertensivity Reactions and Inflammation", *Science*, 220, 568–575 (1983).
Michael K. Bach, "Inhibitors of Leukotriene Synthesis and Action", *The Leukotrienes, Chemistry and Biology,* pp. 163–194 (Academic Press, Inc., 1984).
C. W. Lee, et. al., "Human Biology and Immunoreactivity of Leukotrienes", *Advances in Inflammation Research*, vol. 6, pp. 219–225 (Raven Press, New York 1984).
Editorial, "Leukotrienes and Other Lipoxygenase Products in the Pathogenesis and Therapy of Psoriasis and Dermatoses":, *Arch Dermatol,* 119 541–547 (1983).
Robert A. Lewis, et. al. "A Review of Recent Contributions on Biology Active Products of Archiodonate Conversion", *Int. J. Immunopharmac.,* 4, 85–90 (1982).
Michael K. Bach, *Biochemical Pharmacology,* 33, 515–521 (1984).
E. L. Becker, *Chemotactic Factors of Inflammation,* pp. 223–225 (Elsevier Science Publishers, V. B. Amsterdam, 1983).
P. Sharon and W. F. Stenson, *Gastroenterology,* 84, 454 (1984).
M. W. Mush, et al., *Science,* 217, 1255 (1982).

*Primary Examiner*—Leonard Schenkman
*Attorney, Agent, or Firm*—Mary Jo Kanady; Paul D. Matukaitis

[57] ABSTRACT

The compounds of the present invention comprise substituted phenolic thioethers, sulfoxides, and disulfides that are specific inhibitors of 5-lipoxygenase and which, therefore, are useful in the treatment of local and systemic inflammation, allergy and hypersensitivity reactions and other disorders in which agents formed in the 5-lipoxygenase metablic pathway are involved.

25 Claims, No Drawings

PHENOLIC THIOETHERS, SULFOXIDES, AND DISULFIDES AS INHIBITORS OF 5-LIPOXYGENASE

This is a continuation of application Ser. No. 07/058,457, filed June 5, 1987.

BACKGROUND OF THE INVENTION

The present invention relates to substituted phenolic thioethers, sulfoxides, and disulfides and more particularly relates to the novel compounds of formula I which are specific 5-lipoxygenase inhibitors and are useful, for example, as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion and possibly that of tumor cells (metastasis). $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of LTB . $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases. Examples of such proteases include elastase, cathepsin G, collagenase and the like.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with protease inhibitors and/or cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, inflammatory bowel disease, nephritis, vasculitis, adult respiratory distress syndrome (ARDS) and other allergic, hypersensitivity, and inflammatory conditions.

See Bengt Samuelsson, "Leukotrienes: Mediators of Immediate Hypersensitivity Reactions and Inflammation", *Science*, 220, 568–575 (1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, 119, 541–547 (1983); Robert A. Lewis et al., "A Review of Recent Contributions on Biologically active Products of Arachidonate Conversion", *Int. J. Immunopharmac.*, 4, 85–90 (1982); Michael K. Bach, *Biochemical Pharmacology*, 23, 515–521 (1984); and E. L. Becker, *Chemotactic Factors of Inflammation*, pp 223–225 (Elsevier Science Publishers V.B., Amsterdam, 1983); P. Sharon, and W.F. Stenson, *Gastroenterology*, 84, 454 (1984); and M.W. Musch, et al., *Science*, 217, 1255 (1982).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Hypolipidemic 2-(3,5 di-tert-butyl-4-hydroxyphenyl) thioalkanoic acids and esters are disclosed in Wagner, et al., J. MED CHEM., 1977, Vol. 20, No. 8, p 1007–1013.

CA 82(7):43065k discloses (3,5-di-tert-butyl-4-hydroxyphenylthio) acetic acid esters.

CA 96(20):173323t, CA 94(5):30290c, and CA 86(1):5066m disclose [[(3,5-bis(1,1-dimethylethyl)-4-hydroxyphenyl]thio]acetic acid.

CA 87(14):102880a discloses 3-[[3,5-bis(1,1-dimethylethyl)-4-hydroxyphenyl]thio]propanoic acid.

U.S. Pat. No. 4,012,523 discloses hypolipidemic 2-[3,5-di-tert-butyl-4-hydroxyphenyl(thio or sulfonyl)-]alkanoic acids and derivatives.

[(Di-tert-butylhydroxyphenyl)thio]alkanoic acids are also disclosed in CA 85(19):12854k, CA 85(3):14147v, and CA 81(23):151815t.

U.S. Pat. Nos. 4,029,812, 4,076,841 and 4,078,084 disclose compounds of the formula

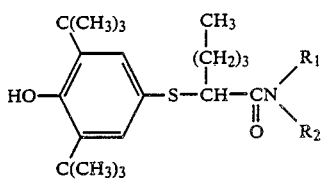

comprising 2-(3,5-di-tert-butyl-4-hydroxyphenyl) thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., Izv. Vyssh. Uchebn. Zaved., Khim. Khim. Tekhnol., 20, 568–574 (1977). The compounds resulting from the foregoing process have the general formulas $RS(CH_2)_nX$ and $S(CH_2CH_2X)_2$ in which R is 3,5-di-tert-butyl-4-hydroxyphenyl and X represents, for example, —C≡N, $NH_2$, $CH(OH)CH_2Cl$, OH, COCl, and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

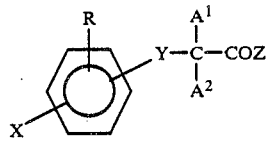

wherein, when Y is sulfur, X is hydrogen, benzyl, benzyloxy, benzylthio, or substituted derivatives thereof; R is hydrogen halogen, hydroxy, alkyl, or alkoxy; $A^1$ and $A^2$ are hydrogen or alkyl; and Z is amine, azacyclohydrocarbyloxy, alkoxy of 1–4 carbons, hydroxy, $0-M^+$ where M is a cation, cycloalkoxy of 3–6 ring carbons, tertiaryaminoalkoxy, pivaloyloxyalkoxy, or pyridyl-C-alkoxy.

SUMMARY OF THE INVENTION

It is, therefore, a primary object of the present invention to provide novel substituted phenolic thioethers.

It is a further object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide unit dosage forms adapted for, e.g., oral or parenteral administration. Such dosage forms would be useful in the treatment, management, and mitigation of allergies, inflammation, hypersensitivity reactions, and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the compositions and methods of the invention comprised of compounds of the formula

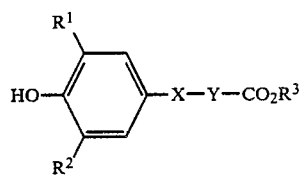

or a pharmaceutically acceptable base addition salt thereof; wherein $R^1$ and $R^2$ are independently $C_4$-$C_{10}$ tert-alkyl;

X is:
(a) —S—;
(b) —(SO)—; or
(c) —S—S—;

Y is:
(a) $C_1$-$C_6$ alkylene; or
(b) $C_2$-$C_6$ alkenylene, with the proviso that the double bond is not on a carbon adjacent to X; and $R^3$ is:
(a) hydrogen; or
(b) $C_1$-$C_6$ alkyl; or $R^3$ and Y together with —$CO_2$ are

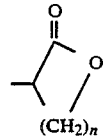

wherein n is 2 or 3.

The term "$C_1$-$C_6$ alkyl" refers to straight or branched chain alkyl groups having from 1 to 6 carbon atoms also referred to as lower alkyl. Examples of $C_1$-$C_6$ alkyl are methyl, ethyl, propyl, butyl, pentyl, hexyl, and the isomeric forms thereof.

The term "$C_4$-$C_{10}$ tert-alkyl" as used herein in reference to $R^1$ and R2 refers to branched chain alkyl moieties of from about 4 to 10 carbon atoms having a tertiary carbon atom attached to the phenyl ring substituted $R^1$ and $R^2$. Examples of such groups are tert-butyl (i.e., 1,1-dimethylethyl), 1,1-dimethylpropyl, 1-methyl-1-(ethyl)pentyl, 1,1-diethylpropyl, 1-ethyl-1-(propyl)butyl, and the like.

The term "$C_1$-$C_6$ alkylene" refers to straight or branched chain alkylene chains having from 1 to 6 carbon atoms. Examples of $C_1$-$C_6$ alkylene are methylene, ethylene, trimethylene, tetramethylene, pentamethylene, hexamethylene, and the isomeric forms thereof.

The term "$C_2$-$C_6$ alkenylene" refers to straight or branched chain alkenylene chains having from 2 to 6 carbon atoms. Examples of $C_2$-$C_6$ alkenylene are ethenylene, propenylene, butenylene, pentenylene, hexenylene, and the isomeric forms thereof The term "pharmaceutically acceptable base addition salt" refers to a salt prepared by contacting a compound of Formula I with a base whose cation is generally considered suitable for human consumption. Examples of pharmaceutically acceptable addition salts include lithium, sodium, potassium, magnesium, calcium, titanium, ammonium, alkylammonium, dialkylammonium, trialkylammonium, tetraalkylammonium, triethanolamine, lysine, and guanidinium salts.

It will be appreciated by those skilled in the art that when Y in Formula I represents branched chain alkylene or alkenylene or X is —(SO)—, an asymmetric center may exist and accordingly enantiomers or diastereomers and mixtures may be obtained. The present invention includes such mixtures as well as the separate isomers.

The preferred embodiments of this invention include compounds of the following general structure:

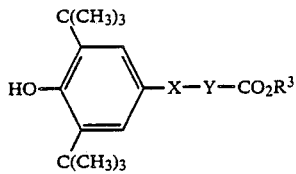

or a pharmaceutically acceptable base addition salt thereof; wherein X is —S—, —(SO)—, or —S—S—; Y is $C_1$-$C_6$ alkylene or $C_2$-$C_6$ alkenylene, with the proviso that the double bond is not on a carbon adjacent to X; and $R^3$ is hydrogen or $C_1$-$C_6$ alkyl; or wherein X is —S—, —(SO)—, or —S—S—; and $R^3$ and Y together with —$CO_2$ are

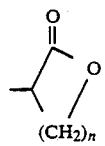

wherein n is 2 or 3.

The most preferred embodiments of this invention include compounds of the following general structure:

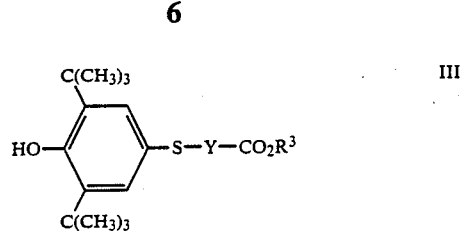

wherein Y is $C_1$-$C_6$ alkylene; and $R^3$ is hydrogen or $C_1$-$C_6$ alkyl.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. the dosage regimen utilizing the present compounds is selected in accordance with a variety of factors including the type, age, weight, sex, and medical condition of the patient; the severity of the condition to be ameliorated; and the route of administration A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses two to four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture Suitable binders include starch, gelatin, natural sugars, corn sweeteners, natural and synthetic gums such as acacia, sodium alginate, carboxymethylcellulose, polyethylene glycol, and waxes Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of this invention may be prepared by the methods illustrated in the following Schemes Unless otherwise specified, the various substituents are defined as for Formula I, above. Scheme A illustrates a general method for preparing substituted phenolic thioethers of this invention.

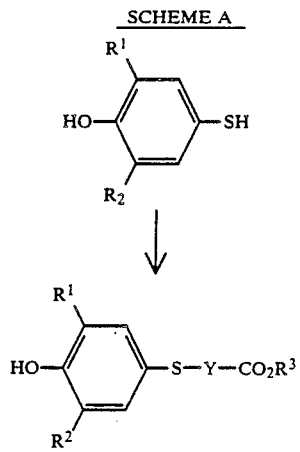

Alkylation of disubstituted 4-mercaptophenols of Formula IV with suitable alkylating reagents using methods known to those skilled in the art yields thioethers of Formula V. Preferred alkylation conditions involve stirring a compound of Formula IV with a suitable alkylating reagent in a suitable organic solvent containing a suitable base. Suitable alkylating reagents include halo compounds of the formula halogen-Y-$CO_2R^3$, where the halogen is preferably bromine, with the proviso that where Y is alkenylene, the halogen atom of halogen-Y-$CO_2R^3$ may not be attached directly to a carbon-carbon double bond For compounds of Formula V in which Y is —$C(R^3)_2$-$C(R^3)_2$—, alkylation may also be effected using acrylates of the formula $C(R^3)_2$=$C(R^3)_2$-$CO_2R^3$. Suitable organic solvents are organic liquids in which reactants may be dissolved or suspended but which are otherwise chemically inert. Examples of suitable organic solvents include lower alcohols, such as methanol, ethanol, or propanol; ketones, such as acetone or methyl ethyl ketone; esters, such as ethyl acetate; ethers and cyclic ethers, such as tetrahydrofuran; and other solvents known in the art. Preferred organic solvents include alcohols, acetone, and tetrahydrofuran Suitable bases for the reaction are chemical compounds that are sufficiently basic to prevent the reaction medium from becoming acidic but which do not themselves form significant quantities of by-products by reaction with other chemical reagents or with reaction products. Examples of suitable bases include alkali metal bicarbonates, such as lithium, sodium, or potassium bicarbonate; alkali metal carbonates, such as lithium, sodium, or potassium carbonate; alkali metal hydroxides such as lithium, sodium or potassium hydroxide; alkali metal alkoxides, such as lithium, sodium, or potassium methoxide or ethoxide; alkaline earth carbonates, such as calcium carbonate or barium carbonate; and tertiary amines, such as triethylamine, tributylamine, N-methylmorpholine, and the like. Preferred bases include sodium ethoxide or triethylamine. Compounds of Formula V in which $R^3$ is $C_1$-$C_6$ alkyl may be converted to free acids of Formula V (in which $R^3$ is hydrogen) using any of several methods known in the art.

Using the same general method, lactones of Formula VI may be prepared by the reaction of disubstituted 4-mercaptophenols of Formula IV with 2-halogen-substituted lactones.

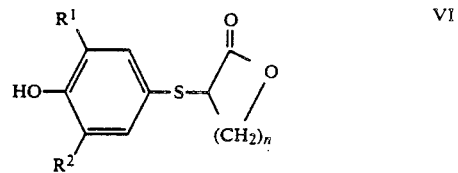

Scheme B illustrates a method for preparing certain alkenylene compounds, Formula VIII, of this invention.

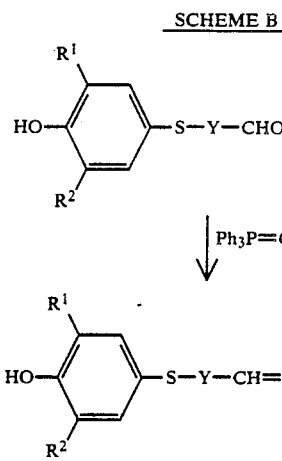

An aldehyde of Formula VII, where Y is defined as above, may be extended to form an alkenylene compound of Formula VIII by reaction with a (carboalkoxymethylene)triphenylphosphorane of the formula $Ph_3P$=$CR^3CO_2R^3$ where $R^3$ is defined as above or other similar phosphorus-containing reagents. Preferred reaction conditions involve the reaction in a suitable organic solvent under an inert atmosphere of a compound of Formula VII with (carbethoxymethylene)triphenylphosphorane. Suitable organic solvents are organic liquids in which reactants may be dissolved or suspended but which are otherwise chemically inert. Examples of suitable organic solvents include alkanes and cycloalkanes; ethers and cyclic ethers; aromatic hydrocarbons, such as benzene or toluene; and other solvents known in the art. Preferred organic solvents include benzene and toluene.

The aldehydes (VII) in Scheme B can be prepared by Michael Addition to an acrolein derivative in the manner presented for the acrylatic esters in Scheme A. Other aldehydes can be prepared from the corresponding halo-aldehyde or protected halo aldehyde by alkylation in the presence of a base as is discussed for Scheme A. Suitable protecting groups are well known in the art and include ethylene acetals, dimethylacetals and the like. The protecting groups can be removed with acids such as hydrochloric acid, acetic acid, trifluoroacetic acid and the like.

Scheme C illustrates a method for preparing disulfide compounds, Formula IX, of this invention.

SCHEME C

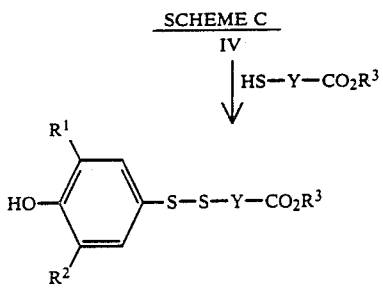

Coupling disubstituted 4-mercaptophenols of Formula IV with suitable mercaptans of the formula HS-Y-$CO_2R^3$ using methods known to those skilled in the art yields disulfides of Formula IX. Preferred coupling conditions involve stirring the 4-mercaptophenol and the mercaptan in a suitable organic solvent in the presence of atmospheric oxygen. Suitable organic solvents for the coupling reaction are organic liquids in which reagents may be dissolved or suspended but which are otherwise chemically inert. Examples of suitable organic solvents include alkanes and cycloalkanes; ethers and cyclic ethers; aromatic hydrocarbons; halocarbons, such as chloroform, dichloromethane, ethylene dichloride, and the like; and other solvents known in the art. A preferred organic solvent is dichloromethane.

Scheme D illustrates a method for preparing sulfoxides, Formula X, of this invention and sulfones, Formula XI.

SCHEME D

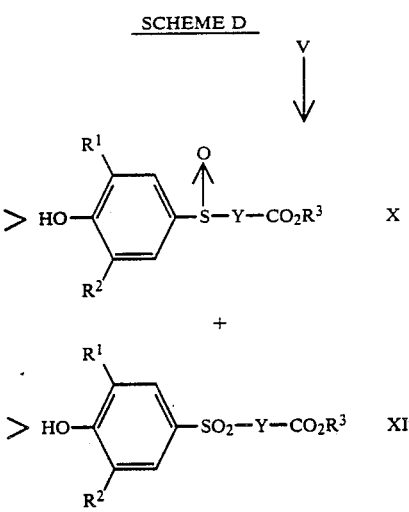

The sulfoxide compounds of this invention, Formula X, may be prepared by oxidation of the thioethers of Formula V using methods known to those skilled in the art. Commonly used oxidizing agents include, for example, peracids such as m-chloroperoxybenzoic acid; percamphoric acid; peresters; peroxides, such as hydrogen peroxide; sodium metaperiodate; selenium dioxide; manganese dioxide; iodosobenzene; and the like. Optically active oxidants can provide optically active sulfoxides. Preferred conditions for preparing sulfoxides of Formula X include oxidizing thioethers V with an approximately equimolar quantity of m-chloroperoxybenzoic acid in a suitable organic solvent. Suitable organic solvents for the oxidation include alkanes and cycloalkanes; aromatic hydrocarbons; halocarbons, such as chloroform, dichloromethane, ethylene dichloride, and the like; and other solvents known in the art. A preferred organic solvent is dichloromethane. Oxidation may then be quenched by adding dimethylsulfide or potassium bisulfite. The sulfoxides of Formula X may then be isolated and purified by methods known in the art, including recrystallization and chromatography.

Further oxidation of the sulfoxide compounds of Formula X yields corresponding sulfones of Formula XI. The sulfones may form in situ during the initial oxidation reaction of thioethers of Formula V, especially if two equivalents of oxidant are used, or may be prepared by a separate oxidation of isolated sulfoxides of Formula X. The sulfones of Formula XI may then be isolated and purified by methods known in the art, including recrystallization and chromatography. Where the sulfones of Formula XI are prepared along with sulfoxides of Formula X during the initial oxidation reaction, the preferred method of isolation is chromatography.

The following non-limiting examples further illustrate details for the preparation of the compounds of the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

EXAMPLE 1

3,5-bis(1,1-dimethylethyl)-4-hydroxyphenyl thiocyanate

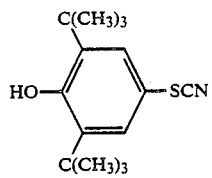

A mixture of 2,6-di-tert-butylphenol (474g, 2.30 mole) and ammonium thiocyanate (76.12 g, 4.83 mole) in methanol (1200ml) was stirred with cooling at 0° C. While the temperature was maintained at 0 to 10° C, chlorine gas was slowly bubbled through the mixture for about 1 hour, during which time the reaction mixture became a heterogeneous yellow color. Ammonia was then bubbled through the mixture for about 1.5 hours, during which time the reaction mixture was maintained at a temperature of between 0 to 10° C. The reaction was stirred for an additional hour at 0° C., poured into a 2 liters of cold distilled water and refrigerated overnight. The aqueous phase was decanted, and the solid was taken up in methanol, precipitated by addition of water, filtered, and dried for 2 days over phosphorus pentoxide. The resulting gummy yellow solid was recrystallized from pentane and dried in vacuo to yield the product as a white powder, m.p. 61.5°–63° C.

Analysis Calcd. for $C_{15}H_{21}NSO$:
Theory: C, 68.40; H, 8.03; N, 5.32; S, 12.17.
Found: C, 68.85; H, 8.05; N, 5.29; S, 12.12.

EXAMPLE 2

2,6-bis(1,1-dimethylethyl)-4-mercaptophenol

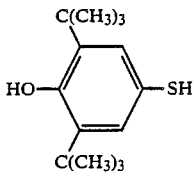

3,5-Bis(1,1-dimethylethyl)-4-hydroxyphenylthiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica The fractions containing the thiol were combined and the solvents removed to yield a white powder Recrystallization from methanol/water yielded, upon drying, 43.3 g of the title compound. The NMR spectrum confirmed the identity of the product.

EXAMPLE 3

4-[[3,5-bis(1,1-dimethylethyl)-4-hydroxyphenyl]thio]-butanoic acid

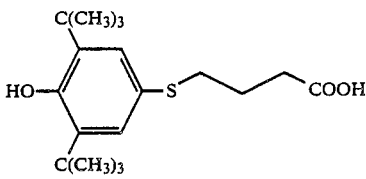

To a solution of 2,6-bis(1,1-dimethylethyl)-4-mercaptophenol (3.57 g, 15 mmole) and ethyl 4-bromobutyrate (3.23 g, 16.5 mmole) in 10 ml of acetone was added potassium hydroxide flakes (2.52 g, 45 mmole) Water (20 ml) was added and the solution was stirred for 1.5 hours, then concentrated in vacuo to dryness. Water (50 ml) was added to the residue and the aqueous mixture was washed with three portions (75 ml each) of ethyl acetate. The aqueous layer was separated and acidified with concentrated hydrochloric acid and extracted with two portions (50 ml each) of ethyl acetate. The organic layers were combined and washed with water, dried over sodium sulfate, filtered and concentrated in vacuo to an oil. Purification by chromatography on silica gel and recrystallization from diethyl ether-hexane yielded, after collection and drying in vacuo, the title compound, m.p. 112°–113.5°.

Analysis Calcd. for $C_{18}H_{28}SO_3$: C, 66.63; H, 8.70; S, 9.88.

Found: C, 66.71; H, 8.74; S, 9.57.

EXAMPLE 4

5-[[3,5-bis(1,1-dimethylethyl)-4-hydroxyphenyl]thio]-pentanoic acid

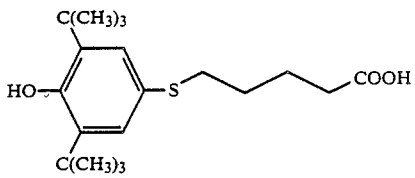

To a solution of freshly prepared sodium ethoxide (ca. 24 mmole) in ethanol (30 ml) was added 2,6-bis(1,1-dimethylethyl)-4-mercaptophenol (2.9 g, 12 mmole), followed by 5-bromovaleric acid (2.0 g, 11 mmole). The reaction mixture was stirred at room temperature for 20 hours and poured into water (50 ml) containing 1N hydrochloric acid (40 ml). The acidic mixture was extracted with diethyl ether (100 ml) and the ether layer was dried over magnesium sulfate, filtered, and concentrated in vacuo to an oil. Chromatography on silica gel and recrystallization from aqueous ethanol gave the title compound, m.p. 104°–105°.

Analysis Calcd. for $C_{19}H_{30}SO_3$: C, 67.40; H, 8.95; S, 9.47.

Found: C, 67.80; H, 9.03; S, 9.69.

EXAMPLE 5

Ethyl 2-[[3,5-bis(1,1-dimethylethyl)-4-hydroxyphenyl]thio]-propanoate

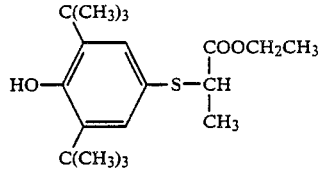

To a solution of 2,6-bis(1,1-dimethylethyl)-4-mercaptophenol (2.0 g, 8.4 mmole) and ethyl 2-bromopropanoate (1.52 g, 8.4 mmole) in tetrahydrofuran (50 ml) was added triethylamine (0.85 g, 8.4 mmole) The mixture was stirred at room temperature for 20 hours. Solids were removed by filtration and the filtrate was added to diethyl ether (75 ml) and then washed with 1 N hydrochloric acid (50 ml), dried over magnesium sulfate, filtered, and concentrated in vacuo to an oil. Chromatography on silica gel gave the title compound Analysis Calcd. for $C_{19}H_{30}SO_3$: C 67.40; H 8.95; S, 9.47.

Found: C, 67.76; H, 8.93; S, 9.44.

EXAMPLE 6

2-[[3,5-bis(1,1-dimethylethyl)-4-hydroxyphenyl]thio]-propanoic acid

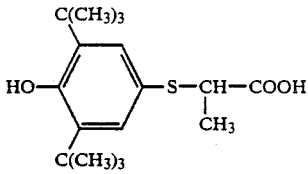

To a solution of ethyl 2-[[3,5-bis(1,1-dimethylethyl)-4hydroxyphenyl]thio]propanoate (1.16 g, 3.4 mmole) from Example 5 in absolute ethanol (20ml) was added lithium hydroxide hydrate (0.2g, 4.8 mmole). Water was added until the solution became cloudy and the mixture was then stirred for 20 hours Additional lithium hydroxide hydrate (0.75 g, 17.9 mmole) was added and the mixture was stirred for another two hours. The mixture was poured into 0.5 N hydrochloric acid (75 ml) and extracted with diethyl ether (100 ml in two portions). The ether extract was dried over magnesium sulfate, filtered, and concentrated in vacuo to a solid. Recrystallization from hexane gave the title compound, m.p. 110°-113°.

Analysis Calcd. for $C_{17}H_{26}SO_3$: C, 65.77; H, 8.44; S, 10.33.

Found: C, 65.64; H, 8.41; S, 10.37.

EXAMPLE 7

Ethyl 2-[[3,5-bis(1,1-dimethylethyl)-4-hydroxyphenyl]thio]-pentanoate

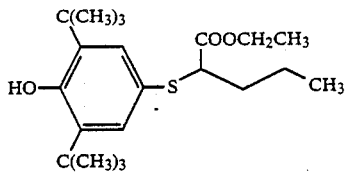

To a solution of 2,6-bis(1,1-dimethylethyl)-4-mercaptophenol (2.38 g, 0.01 mole) and ethyl 2-bromopentanoate (2.09 g, 0.01 mole) in acetone (100 ml) was added potassium hydroxide flakes (1.68 g, 0.03 mole) The mixture was stirred at room temperature for one hour and then concentrated in vacuo to an oil. The oil was added to water (50 ml) and extracted with diethyl ether, dried over sodium sulfate, filtered, and concentrated in vacuo to an oil. Chromatography on silica gel gave the title compound.

Analysis Calcd. for $C_{21}H_{34}SO_3$: C, 68.81; H, 9.35; S, 8.75.

Found: C, 69.05; H, 9.34; S, 8.70.

EXAMPLE 8

2-[3,5-bis(1,1-dimethylethyl)-4-hydroxyphenyl]thio]-pentanoic acid

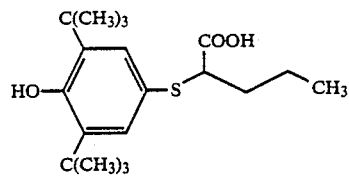

The title compound was prepared by the method of Example 6 using ethyl 2-[[3,5-bis(1,1-dimethylethyl)-4-hydroxyphenyl]thio]pentanoate instead of ethyl 2-[[3,5-bis(1,1-dimethylethyl)-4-hydroxyphenyl]thio]propanoate.

Analysis Calcd. for $C_{19}H_{30}SO_3$: C, 67.42; H, 8.93; S, 9.47.

Found: C, 67.39; H, 9.13; S, 9.69.

EXAMPLE 9

Methyl 3-[[3,5-bis(1,1-dimethylethyl)-4-hydroxyphenyl]thio]-propanoate

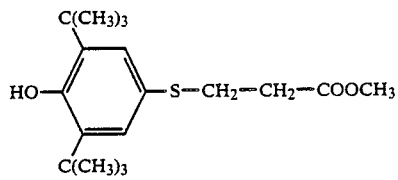

To a solution of 2,6-bis(1,1-dimethylethyl)-4-mercaptophenol (5.00 g, 0.021 mole) and triethylamine (0.5 ml) in methanol (50 ml) was added methyl acrylate (5.40 g, 0.063 mole). The mixture was stirred under argon at room temperature for about 20 hours. Volatiles were removed in vacuo to give an oil. Chromatography on silica gel and recrystallization from hexane gave the title compound, m.p. 63.5°-65.5°.

Analysis Calcd. for $C_{18}H_{28}SO_3$: C, 66.62; H, 8.70; S, 9.88.

Found: C, 66.93; H, 8.62; S, 9.87.

EXAMPLE 10

Methyl 3-[[3,5-bis(1,1-dimethylethyl)-4-hydroxyphenyl]sulfinyl]propanoate

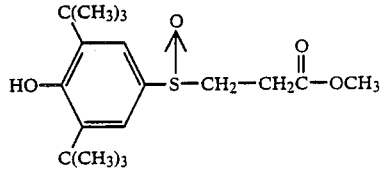

A mixture of methyl 3-[[3,5-bis(1,1-dimethylethyl)-4-hydroxyphenyl]thio]propanoate (0.5 g, 1.5 mmole) and meta-chloroperoxybenzoic acid (0.32 g, 1.5 mmole) in dichloromethane (25 ml) was stirred under argon for 12 hours. Excess peroxide was destroyed with saturated aqueous potassium bisulfite and the phases were separated. The organic layer was washed with water, dried over magnesium sulfate, filtered, and concentrated in vacuo to dryness Recrystallization from diethyl ether and dichloromethane gave the title compound m.p. 106°-108°.

Analysis Calcd. for $C_{18}H_{28}SO_4$: C, 63.50; H, 8.29; S, 9.42.

Found: C, 63.60; H, 8.28; S, 9.45.

EXAMPLE 11

Methyl 3-[[3,5-bis(1,1-dimethylethyl)-4-hydroxyphenyl]sulfonyl]propanoate

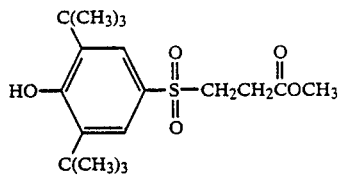

The title compound, m.p. 109°-111°, was prepared by the method of Example 10 using methyl 3-[[3,5-bis(1,1 dimethylethyl)-4-hydroxyphenyl]sulfinyl]propanoate (0.4 g, 1.23 mmole) instead of methyl 3-[[3,5-bis(1,1-dimethylethyl)-4-hydroxyphenyl]thio]propanoate.

Analysis Calcd. for $C_{18}H_{28}SO_5$: C, 60.65; H, 7.92; S, 8.99.

Found: C, 60.65; H, 8.12; S, 9.01.

EXAMPLE 12

3-[[3,5-bis(1,1-dimethylethyl)-4-hydroxyphenyl)thio]propanoic acid

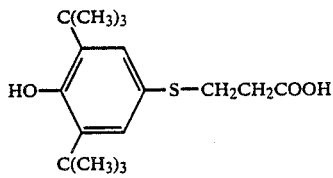

Methyl 3-[[3,5-bis(1,1-dimethylethyl)-4-hydroxyphenyl]thio]propanoate (1.0 g, 3 mmole) was added to a clear solution of lithium hydroxide hydrate (0.64 g, 15 mmole) in methanol (15 ml). Water was added until the solution became cloudy and the mixture was then stirred overnight. The mixture was concentrated to about 10 ml and acidified with cold (5°) 10% hydrochloric acid. The resultant precipitate was collected by filtration, washed with water, and air dried Recrystallization from cyclohexane gave the title compound, m.p. 108°-110°.

Analysis Calcd for $C_{18}H_{26}SO_3$: C, 65.77; H, 8.44; S, 10.33.

Found: C, 65.80; H, 8.61; S, 10.45.

EXAMPLE 13

Ethyl 5-[[3,5-bis(1,1-dimethylethyl)-4-hydroxyphenyl]thio]-2-pentenoate

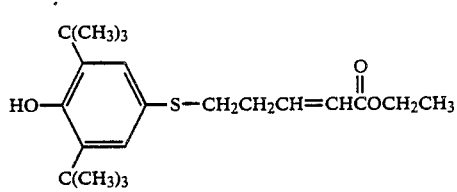

Triethylamine (1.1 ml, 7.6 mmole) was added to a solution of 2,6-bis(1,1-dimethylethyl)-4-mercaptophenol (18.2 g, 76 mmole) in methanol (200 ml) and stirred for 30 minutes. Freshly distilled acrolein (12.8 g, 0.23 mole) was added and the solution stirred at room temperature. Chromatography on silica gave 3-[[3,5-bis(1,1-dimethylethyl)-4-hydroxyphenyl]thio]propanal. To a solution of the aldehyde (2.0 g, 6.8 mmole) in benzene (20 ml) under argon was added in one portion (carbethoxymethylene)triphenylphosphorane (2.36 g, 6.8 mmole). The mixture was heated at reflux for 20 hours, allowed to stand at room temperature for three days, and then concentrated in vacuo to an oil. Chromatography on silica gel gave the title compound.

Analysis Calcd for $C_{21}H_{32}SO_3$: C, 69.19; H, 8.85; S, 8.79.

Found: C 69.06; H, 8.96; S, 8.75.

EXAMPLE 14

Methyl [[3,5-bis(1,1-dimethylethyl)-4-hydroxyphenyl]dithio]acetate

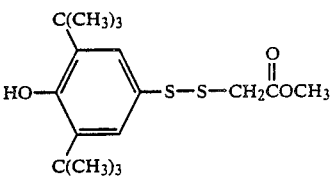

To a solution of sodium ethoxide, freshly prepared from sodium (1.31 g, 57.2 mmole) in ethyl alcohol (200 ml), was added 2,6-bis(1,1-dimethylethyl)-4-mercaptophenol (6.8 g, 28.6 mmole) and the mixture was stirred for one hour. After cooling to 5° C. with an ice bath, 1,1-dimethylethylene oxide (2.06 g, 28.6 mmole) was added and the ice bath removed. After stirring for 5.5 hours the reaction mixture was poured into 10% hydrochloric acid. The ethyl alcohol was removed in vacuo and the aqueous residue was extracted with ethyl acetate. The extracts were combined, dried over sodium sulfate, filtered, and concentrated to give 2,6-bis (1,1-dimethylethyl)-4-[(2-hydroxy-2-methylpropyl)thio]-phenol. Trifluoroacetic acid (3 ml) was added to a solution of the phenol intermediate (2.2 g, 7 mmole), followed by addition by syringe of methyl thioglycolate (0.7 g, 6.7 mmole). After three hours the mixture was poured into water (100 ml) and extracted with ethyl acetate. The organic layer was dried over sodium sulfate, filtered, and concentrated in vacuo to an oil. Chromatography on silica gel gave the title dithio compound, m.p. 64°-68°.

Analysis Calcd. for $C_{17}H_{26}S_2O_3$: C, 59.61; H, 7.65; S, 18.72.

Found: C, 59.95; H, 7.59; S, 18.79.

EXAMPLE 15

3-[[3,5-bis(1,1-dimethylethyl)-4-hydroxyphenyl]thio]-dihydro-2(3H)-furanone

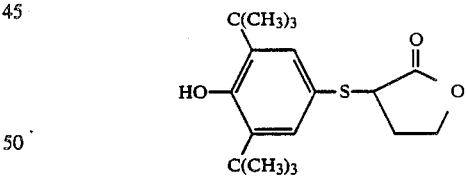

Sodium hydroxide (0.20 g, 5 mmole) was added to a solution of 2,6-bis(1,1-dimethylethyl)-4-mercaptophenol (1.11 g, 4.6 mmole) in methanol (20 ml) and stirred at room temperature until dissolved. 2-Bromobutyrolactone (0.82 g, 5 mmole) was added and the mixture was stirred at room temperature for 48 hours. The mixture was diluted with water, acidified with 1 N hydrochloric acid, and extracted with diethyl ether. The ether extract was washed with water, dried over sodium sulfate, filtered and concentrated in vacuo. The residue was dissolved in a minimum of hexane and cooled to induce crystallization. Chromatography of the solid on silica gel and recrystallization from hexane gave the title compound, m.p. 98°-100°.

Analysis Calcd. for $C_{18}H_{26}SO_3$: C, 67.05; H, 8.13; S, 9.94.

Found: 67.02; H, 8.02; S, 9.94.

BIOLOGICAL EVALUATION

The compounds of the invention are evaluated with respect to 5-lipoxygenase inhibition according to the following assay procedure.

Inhibition of 5-lipoxygenase, vitro: anti-inflammatory, anti-allergy activities The 100,000×g supernatant fraction of Rat Basophilic Leukemia Cell Homogenate (RBL-1) serves as a 5-lipoxygenase enzyme source. The enzyme is incubated with [1-$^{14}$C]-arachidonic acid and $Ca^{++}$ in the presence and absence of test compound. The product of 5-lipoxygenase, 5-hydroxyeicosatetraenoi acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the $IC_{50}$ value (inhibitory concentration to inhibit 50%). The results with respect to certain of the preferred compounds of the present invention are set forth in Table I.

TABLE I

| Compound Example No. | 5-Lipoxygenase Inhibition, in vitro. $IC_{50}$ ($\mu$M) |
|---|---|
| 3 | 1.00 |
| 4 | 1.10 |
| 5 | 0.39 |
| 7 | 1.30 |
| 8 | 6.60 |
| 9 | 0.38 |
| 10 | 16.50 |
| 11 | Inactive |
| 12 | 3.40 |
| 13 | 0.26 |
| 14 | 0.40 |
| 15 | 0.62 |

It is further noted that the compounds of the present invention have not been found to be effective inhibitors of either 12- or 15-lipoxygenases or of cyclooxygenase at concentrations which inhibit 5-lipoxygenase further confirming the specificity of the present compounds for 5-lipoxygenase.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A method for treating lipoxygenase mediated conditions in mammals comprising administering to a mammal in need of such treatment a therapeutically effective amount of a compound of the formula

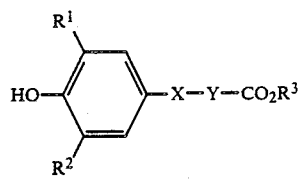

or a pharmaceutically acceptable base addition salt thereof; wherein $R^1$ and $R^2$ are independently $C_4$-$C_{10}$ tert-alkyl;

X is:
 (a) —S—;
 (b) —(SO)—; or
 (c) —S—S—;

Y is:
 (a) $C_1$-$C_6$ alkylene; or
 (b) $C_2$-$C_6$ alkenylene, with the proviso that the double bond is not on a carbon adjacent to X; and $R^3$ is:
 (a) hydrogen; or
 (b) $C_1$-$C_6$ alkyl; or $R^3$ and Y together with —$CO_2$ are

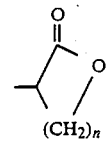

wherein n is 2 or 3.

2. A method according to claim 1 wherein said compound has the formula:

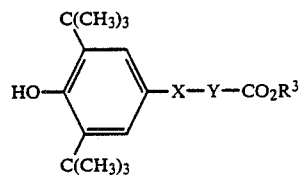

or a pharmaceutically acceptable base addition salt thereof; wherein X is:
 (a) —S—;
 (b) —(SO)—; or
 (c) —S—S—;

Y is:
 (a) $C_1$-$C_6$ alkylene; or
 (b) $C_2$-$C_6$ alkenylene, with the proviso that the double bond is not on a carbon adjacent to X; and $R^3$ is:
 (a) hydrogen; or
 (b) $C_2$-$C_6$ alkyl; or $R^3$ and Y together with —$CO_2$ are

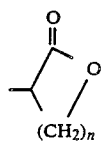

wherein n is 2 or 3.

3. A method according to claim 2 wherein said compound has the formula:

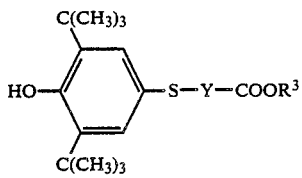

or a pharmaceutically acceptable base addition salt thereof; wherein Y is:
 (a) $C_1$–$C_6$ alkylene; or
 (b) $C_2$–$C_6$ alkenylene, with the proviso that the double bond is not on a carbon adjacent to S; and
$R^3$ is:
 (a) hydrogen; or
 (b) $C_1$–$C_6$ alkyl; or
$R^3$ and Y together with —COO are

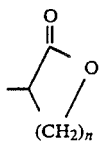

wherein n is 2 or 3.

4. A method according to claim 3 wherein Y is alkylene.

5. A method according to claim 4 wherein $R^3$ is hydrogen

6. A method according to claim 5 wherein said compound is selected from the group consisting of:
4-[[3,5-bis(1,1-dimethylethyl)-4-hydroxyphenyl]thio]-butanoic acid,
5-[[3,5-bis(1,1-dimethylethyl)-4-hydroxyphenyl]thio]-pentanoic acid,
2-[[3,5-bis(1,1-dimethylethyl)-4-hydroxyphenyl]thio]-propanoic acid,
2-[[3,5-bis(1,1-dimethylethyl)-4-hydroxyphenyl]thio]-pentanoic acid, and
3-[[3,5-bis(1,1-dimethylethyl)-4-hydroxyphenyl]thio]-propanoic acid.

7. A method according to claim 4 wherein $R^3$ is $C_1$–$C_6$ alkyl.

8. A method according to claim 7 wherein said compound is selected from the group consisting of:
ethyl 2-[[3,5-bis(1,1-dimethylethyl)-4-hydroxyphenyl]thio]propanoate,
ethyl 2-[[3,5-bis(1,1-dimethylethyl)-4-hydroxyphenyl]thio]pentanoate, and
methyl 3-[[3,5-bis(1,1-dimethylethyl)-4-hydroxyphenyl]thio]propanoate.

9. A method according to claim 3 wherein Y is alkenylene.

10. A method according to claim 9 wherein said compound is ethyl 5-[[3,5-bis(1,1-dimethylethyl)-4-hydroxyphenyl]thio]-2-pentenoate.

11. A method according to claim 4 wherein said compound has the formula

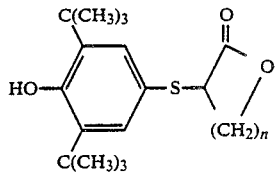

wherein n is 2 or 3.

12. A method according to claim 11 wherein said compound is 3-[[3,5-bis(1,1-dimethylethyl)-4-hydroxyphenyl]thio]dihydro-2(3H)-furanone.

13. A method according to claim 2 wherein said compound has the formula:

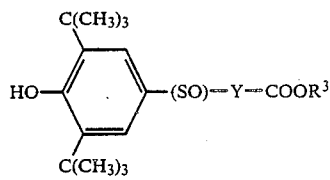

or a pharmaceutically acceptable base addition salt thereof; wherein Y is:
 (a) $C_1$–$C_6$ alkylene; or
 (b) $C_2$–$C_6$ alkenylene, with the proviso that the double bond is not on a carbon adjacent to (SO); and
$R^3$ is:
 (a) hydrogen; or
 (b) $C_1$–$C_6$ alkyl; or
$R^3$ and Y together with —COO are

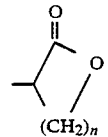

wherein n is 2 or 3.

14. A method according to claim 13 wherein said compound is methyl 3-[[3,5-bis(1,1-dimethylethyl)-4-hydroxyphenyl]sulfinyl]propanoate.

15. A method according to claim 2 wherein said compound has the formula:

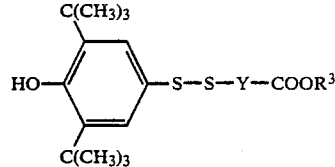

or a pharmaceutically acceptable base addition salt thereof; wherein Y is:
 (a) $C_1$–$C_6$ alkylene; or
 (b) $C_2$–$C_6$ alkenylene, with the proviso that the double bond is not on a carbon adjacent to S; and
$R^3$ is:
 (a) hydrogen; or
 (b) $C_1$–$C_6$ alkyl.

16. A method according to claim 15 wherein said compound is methyl [[3,5-bis(1,1-dimethylethyl)-4-hydroxyphenyl]dithio]acetate.

17. A pharmaceutical composition useful in the treatment of lipoxygenase mediated conditions in mammals comprising a pharmaceutically effective amount of at least one compound of the formula:

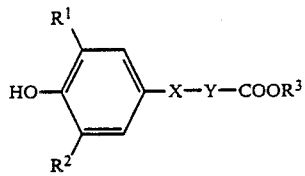

or a pharmaceutically acceptable base addition salt thereof, together with one or more non-toxic pharmaceutically acceptable carriers; wherein $R^1$ and $R^2$ are independently $C_4$–$C_{10}$ tert-alkyl;

X is:
 (a) —S—;
 (b) —(SO)—; or
 (c) —S—S—;

Y is:
 (a) $C_1$–$C_6$ alkylene; or
 (b) $C_2$–$C_6$ alkenylene, with the proviso that the double bond is not on a carbon adjacent to X; and $R^3$ is:
 (a) hydrogen; or
 (b) $C_1$–$C_6$ alkyl; or $R^3$ and Y together with —COO are

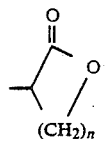

wherein n is 2 or 3; with the proviso that when X is —S—, Y is not $C_1$–$C_6$ alkylene.

18. A pharmaceutical composition according to claim 17 wherein said compound has the formula:

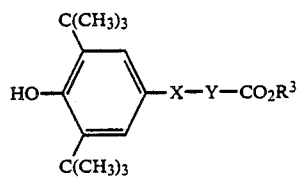

or a pharmaceutically acceptable base addition salt thereof; wherein X is:
 (a) —S—;
 (b) —(SO)—; or
 (c) —S—S—;

Y is:
 (a) $C_1$–$C_6$ alkylene; or
 (b) $C_2$–$C_6$ alkenylene, with the proviso that the double bond is not on a carbon adjacent to X; and $R^3$ is:
 (a) hydrogen; or
 (b) $C_1$–$C_6$ alkyl; or $R^3$ and Y together with —$CO_2$ are

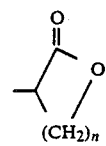

wherein n is 2 or 3; with the proviso that when X is —S—, Y is not $C_1$–$C_6$ alkylene.

19. A pharmaceutical composition according to claim 18 wherein said compound is selected from the group consisting of:

ethyl 5-[[3,5-bis(1,1-dimethylethyl)-4-hydroxyphenyl]-thio]-2-pentenoate,

3-[[3,5-bis(1,1-dimethylethyl)-4-hydroxyphenyl]thio]-dihydro-2(3H)-furanone.

methyl 3-[[3,5-bis(1,1-dimethylethyl)-4-hydroxyphenyl]sulfinyl]propanoate, and methyl[[3,5-bis(1,1-dimethylethyl)-4- hydroxyphenyl]-dithio]acetate.

20. A compound of the formula:

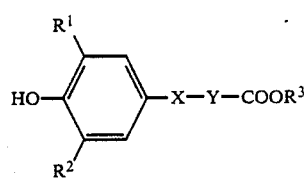

or a pharmaceutically acceptable base addition salt thereof;

wherein $R^1$ and $R^2$ are independently $C_4$–$C_{10}$ tert-alkyl;

X is:
 (a) —S—;
 (b) —(SO)—; or
 (c) —S—S—;

Y is:
 (a) $C_1$–$C_6$ alkylene; or
 (b) $C_2$–$C_6$ alkenylene, with the proviso that the double bond is not on a carbon adjacent to X; and $R^3$ is:
 (a) hydrogen; or
 (b) $C_1$–$C_6$ alkyl; or $R^3$ and Y together with —COO are

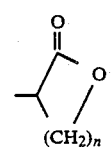

wherein n is 2 or 3; with the proviso that when X is —S—, Y is not $C_1$–$C_6$ alkylene.

21. A compound according to claim 20 of the formula:

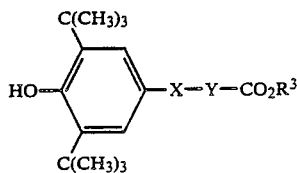

or a pharmaceutically acceptable base addition salt thereof; wherein X is:
(a) —S—;
(b) —(SO)—; or
(c) —S—S—;
Y is:
(a) $C_1$-$C_6$ alkylene; or
(b) $C_2$-$C_6$ alkenylene, with the proviso that the double bond is not on a carbon adjacent to X; and
$R^3$ is:
(a) hydrogen; or
(b) $C_1$-$C_6$ alkyl; or $R^3$ and Y together with —$CO_2$ are

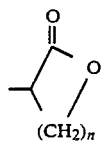

wherein n is 2 or 3; with the proviso that when X is —S—, and Y is $C_1$-$C_6$ alkylene.

22. A compound according to claim 21 which is ethyl 5-[[3,5-bis(1,1-dimethylethyl)-4-hydroxyphenyl]thio]-2-pentenoate.

23. A compound according to claim 21 which is 3-[[3,5-bis(1,1-dimethylethyl)-4-hydroxyphenyl]thio]-dihydro-2(3H)-furanone.

24. A compound according to claim 21 which is methyl 3-[[3,5-bis(1,1-dimethylethyl)-4-hydroxyphenyl]sulfinyl]propanoate, and 25. A compound according to claim 21 which is methyl [[3,5-bis(1,1-dimethylethyl)-4-hydroxyphenyl]-dithio]acetate.

* * * * *